US008683858B2

(12) United States Patent
Piri

(10) Patent No.: US 8,683,858 B2
(45) Date of Patent: Apr. 1, 2014

(54) RECIRCULATING, CONSTANT BACKPRESSURE CORE FLOODING APPARATUS AND METHOD

(75) Inventor: Mohammad Piri, Laramie, WY (US)

(73) Assignee: University of Wyoming, Laramie, WY (US)

( * ) Notice: Subject to any disclaimer, the term of this patent is extended or adjusted under 35 U.S.C. 154(b) by 208 days.

(21) Appl. No.: 13/324,966

(22) Filed: Dec. 13, 2011

(65) Prior Publication Data

US 2012/0211089 A1 Aug. 23, 2012

Related U.S. Application Data

(60) Provisional application No. 61/422,636, filed on Dec. 13, 2010.

(51) Int. Cl.
*G01N 15/08* (2006.01)

(52) U.S. Cl.
USPC ...... 73/152.06; 73/38; 73/152.05; 73/152.08; 73/152.09

(58) Field of Classification Search
USPC ......... 73/38, 152.05, 152.06, 152.08, 152.09, 73/152.11; 324/376
See application file for complete search history.

(56) References Cited

U.S. PATENT DOCUMENTS

| | | | | |
|---|---|---|---|---|
| 3,617,868 A | * | 11/1971 | Beitel et al. | 324/376 |
| 4,304,122 A | * | 12/1981 | Tentor | 73/38 |
| 4,506,542 A | * | 3/1985 | Rose | 73/38 |
| 4,543,821 A | * | 10/1985 | Davis, Jr. | 73/152.07 |
| 4,586,376 A | * | 5/1986 | Outmans | 73/865.8 |
| 4,669,299 A | * | 6/1987 | Closmann | 73/38 |
| 4,868,751 A | | 9/1989 | Dogru et al. | |
| 4,926,128 A | * | 5/1990 | Givens | 324/376 |
| 5,079,948 A | * | 1/1992 | Collins et al. | 73/152.24 |
| 5,095,273 A | * | 3/1992 | Kennedy et al. | 324/376 |
| 5,209,104 A | * | 5/1993 | Collins et al. | 73/38 |
| 5,275,063 A | * | 1/1994 | Steiger et al. | 73/865.6 |
| 5,297,420 A | * | 3/1994 | Gilliland et al. | 73/38 |
| 5,341,101 A | * | 8/1994 | Maerefat et al. | 324/376 |
| 5,345,819 A | * | 9/1994 | Dearing, Jr. | 73/152.23 |
| 5,493,226 A | | 2/1996 | Honarpour et al. | |
| 5,610,524 A | * | 3/1997 | Longeron et al. | 324/376 |
| 5,637,796 A | * | 6/1997 | Deruyter et al. | 73/152.09 |
| 5,698,772 A | * | 12/1997 | Deruyter et al. | 73/38 |
| 7,472,588 B2 | * | 1/2009 | Slavin et al. | 73/152.11 |
| 7,805,982 B2 | * | 10/2010 | Hilab | 73/38 |
| 8,024,960 B2 | * | 9/2011 | Fleury et al. | 73/38 |
| 2010/0126266 A1 | | 5/2010 | Coenen | |
| 2010/0292110 A1 | | 11/2010 | Pope et al. | |

OTHER PUBLICATIONS

International Search Report, International Searching Authority, Apr. 20, 2012, pp. 1-12.

* cited by examiner

*Primary Examiner* — David A Rogers
(74) *Attorney, Agent, or Firm* — Samuel M. Freund; Cochran Freund & Young LLC

(57) ABSTRACT

An apparatus and method for simulating production conditions in hydrocarbon-bearing reservoirs, as an example, by flooding of core samples from such reservoirs, are described. Full recirculation flow measurements permit several fluids (for example, crude oil, brine, and gas) to be simultaneously injected into core samples having varying dimensions. Accurate and stable back pressures are maintained at total flow rates of as high as 200 cc/min., for a large range of fluid viscosities. Accurate and stable net overburden pressures relative to pore pressure are also maintained, thereby simulating the formations at depth. Core samples from formations may also be investigated using the apparatus and method hereof, for carbon dioxide sequestration potential, as another example.

25 Claims, 3 Drawing Sheets

RECIRCULATING, CONSTANT BACKPRESSURE CORE FLOODING APPARATUS AND METHOD

CROSS-REFERENCE TO RELATED APPLICATIONS

The present application claims the benefit of U.S. Provisional Patent Application No. 61/422,636 for "RECIRCULATING, CONSTANT BACKPRESSURE CORE FLOODING APPARATUS AND METHOD" by Mohammad Piri, which was filed on Dec. 13, 2010, the entire content of which is hereby specifically incorporated by reference herein for all that it discloses and teaches.

FIELD OF THE INVENTION

The present invention relates generally to an apparatus and method for characterizing porous materials and, more particularly, to the determination of residual saturation and single and multiphase flow properties such as relative permeabilities, as examples, of core samples from hydrocarbon-bearing reservoirs and other subterranean formations.

BACKGROUND OF THE INVENTION

Permeability is a measure of the ability of fluids to pass through porous media, and is inversely proportional to the flow resistance presented by the medium. When a single fluid saturates the pore space of a medium, measured permeability is known as absolute permeability. For saturations of less than 100%, the measured permeability is termed the effective permeability. Relative permeability is the ratio of effective permeability for a particular fluid at a given saturation to a chosen permeability, and may be determined from measurements of the pressure and fluid saturations. Core flooding measurements for determining material permeability to various fluids as a function of temperature and pressure have been performed using computed tomography (CT) technology. The shape of the fluid fronts can also be monitored when a fluid is driven through a core sample. The images of the cores before and after flooding are subtracted to yield the fluid front interior to the core, without disturbing the sample. Fluid saturation may be measured using x-ray attenuation.

SUMMARY OF THE INVENTION

Embodiments of the present invention overcome the disadvantages and limitations of the prior art by providing an apparatus and method for flooding porous cores with fluids.

Another object of embodiments of the invention is to provide an apparatus and method for flooding porous cores with fluids at constant backpressure.

Yet another object of embodiments of the invention is to provide a device for is to provide an apparatus and method for flooding porous cores with fluids with full-recirculation.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the recirculating, constant backpressure apparatus for flooding a core with at least one chosen fluid, hereof, includes: a core holder for containing the core and having a longitudinal axis, an inlet port for introducing the at least one fluid into contact with the core, an outlet port, and a port for applying a chosen pressure to an exterior surface of the core; an overburden pressure pump in fluid connection with the pressure port of the core holder; at least one fluid pump for pumping the at least one chosen fluid in fluid communication with the inlet port of the core holder; a separator for separating the at least one fluid from the at least one fluid pump by density thereof from other fluids exiting the core holder after having passed through the core, the separator having a first bottom port, a second bottom port, and at least one fluid return port for returning fluid to the at least one fluid pump; a backpressure pump in fluid communication with the outlet port of the core holder for maintaining a chosen back pressure at the outlet port of the core holder, and in fluid communication with the first bottom port of the separator for transferring the at least one fluid exiting said core holder to the separator; and a pressure compensation pump in fluid communication with the second bottom port of the separator for preventing a change in pressure as the at least one fluid is transferred to the separator by the back-pressure pump.

In another aspect of the invention and in accordance with its objects and purposes, the method for flooding a core by recirculating at constant backpressure at least one chosen fluid through said core, hereof, includes the steps of: pumping the least one fluid through a core in a core holder having a longitudinal axis, using at least one fluid pump; pressurizing the exterior surface of the core to a chosen pressure; separating the at least one fluid by density thereof from other fluids exiting the core holder after having passed through the core, in a separator; returning the at least one fluid to the at least one pump, after the step of separating the at least one fluid; maintaining a chosen backpressure for the at least one fluid exiting the core holder; and removing fluid from or adding fluid to the separator to prevent an increase or decrease in backpressure, respectively, in the step of separating the at least one fluid.

Benefits and advantages of embodiments of the present invention include, but are not limited to, providing an apparatus for core-flooding which allows all the fluids to be re-circulated over a large range of flow rates, while an accurate and stable back pressure is maintained, thereby creating a more stable equilibrium between the phases throughout the apparatus, and minimizing the requirement for additional fluids. Accurate regulation of the back pressure also leads to more reliable fluid displacements in the core sample, which in turn leads to more accurate measurements of single and multiphase flow properties (from which the relative permeabilities derive). Further, the pressure and temperature ranges which create miscible or partially miscible fluids and generate unintended saturation variations in the core are reduced, thereby minimizing uncertainties introduced into the measurement of residual saturation during flow experiments.

BRIEF DESCRIPTION OF THE DRAWINGS

The accompanying drawings, which are incorporated in and form a part of the specification, illustrate embodiments of the present invention and, together with the description, serve to explain the principles of the invention.

DETAILED DESCRIPTION OF THE INVENTION

Figure 1:
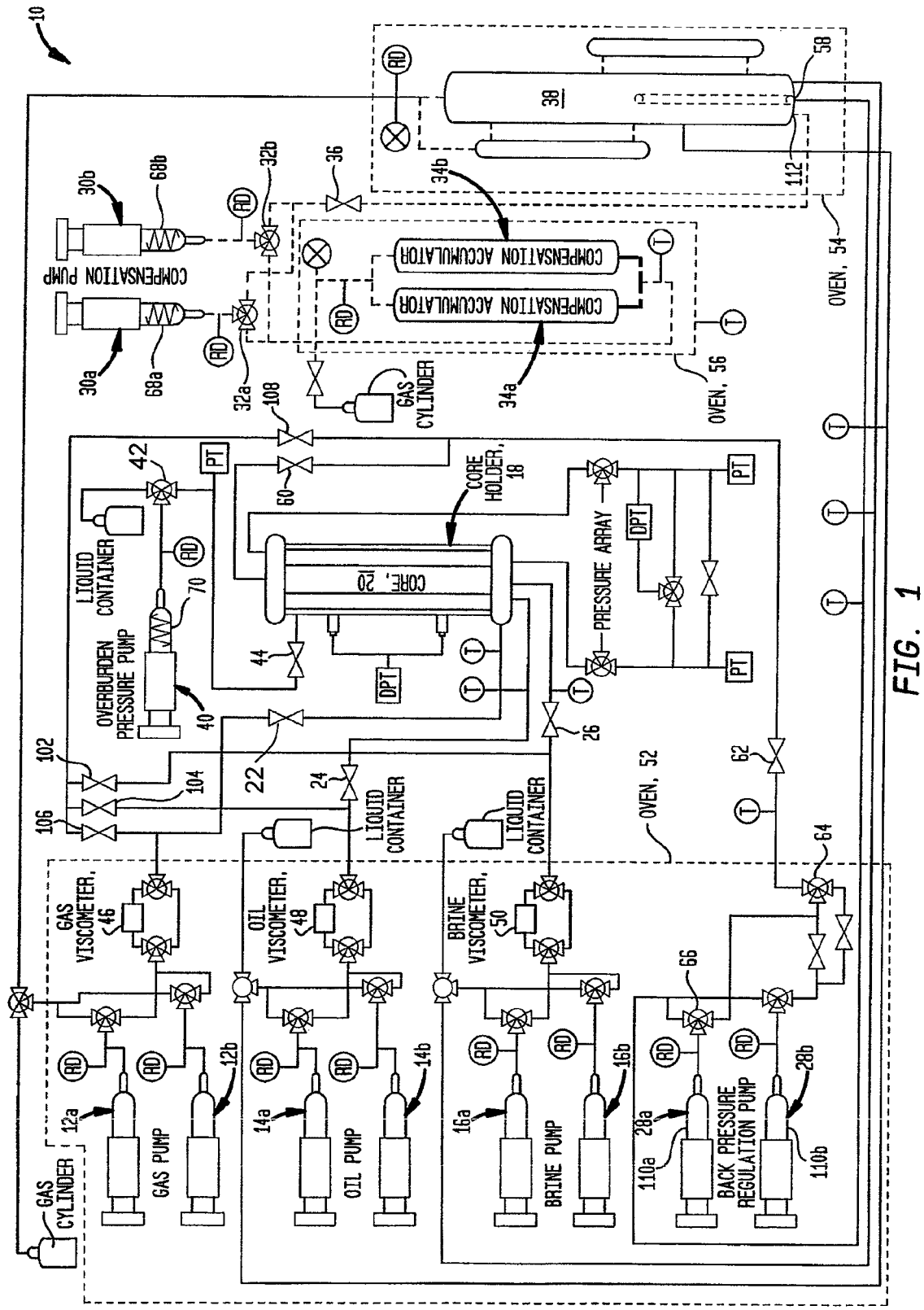
FIG. 1 is a schematic diagram of an embodiment of the apparatus for flooding core samples, while maintaining constant backpressure and recirculating all fluids.

Briefly, embodiments of the present invention include an apparatus and method for simulating production conditions in hydrocarbon-bearing reservoirs by flooding core samples from such reservoirs. Full recirculation flow experiments permit as many as three fluids (for example, crude oil, brine, and gas) to be simultaneously injected into core samples having varying dimensions. Accurate and stable back pressures are maintained at total flow rates of as high as 200 cm$^3$/min. for a large range of fluid viscosities. Accurate and stable net overburden pressure relative to pore pressure is also maintained, thereby simulating the depth of the formation. Core samples from other formations may also be investigated using the apparatus and method hereof, as an example, for carbon dioxide sequestration possibilities. Cores are generally cylindrical in shape.

Three, dual-cylinder injection pumps were used to simultaneously inject three fluids into the core sample in a paired constant flow rate mode.

The fluids produced from the core sample are received by a dual cylinder back pressure regulation pump in a paired constant-pressure receive mode, thereby maintaining accurate and stable back pressure, and generating a stable contact pressure boundary condition at the outlet of the core sample. Produced fluids are then injected into a separator which can simultaneously accept up to three fluids, the lightest fluid residing at the top, the heaviest fluid at the bottom, and the third fluid in the middle. The injection pumps withdraw the fluids for re-injection into the core sample from appropriate locations in the separator. That is, the pumps that inject fluids into the core retract fluids from the separator.

The injection of fluids into the separator by the receiving pump, and the withdrawal of fluids by the injection pumps can, in principle, lead to large variations in the pressure of the separator, particularly at high flow rates or when the volume of the separator is relatively small. This in turn might affect the equilibrium between the phases in the separator, particularly in flow experiments where the pressure and temperature conditions create miscible or partially miscible conditions, and generate unintended saturation variations in the core, thereby introducing uncertainties into the measurement of, for example, the residual saturation during flow experiments.

To reduce such effects, a high-volume, dual-cylinder separator pressure regulator pump is used to maintain the pressure of the separator in a paired, constant-pressure bi-directional mode. Two high-volume high-pressure, high-temperature storage cells are employed, and the fluid levels (that is, the location of oil/water and gas/oil interfaces) in the separator are detected using guided-wave radar liquid level and interface transmitters. This ensures that each injection pump withdraws the correct fluid by maintaining the level of fluids away from the withdrawal ports of the separator. When the pressure of the separator rises above a chosen set point (usually the same or close to the back pressure provided by the back pressure regulating pump), the separator pressure regulator pump rapidly withdraws some of the heaviest fluid from the bottom of the separator. Further, if the pressure of the separator falls below the set point, the separator pressure regulating pump will quickly inject some of the heaviest fluid into the separator. During this pressure maintenance operation, if the separator pressure regulating pump is required to store or obtain fluid, as stated, two high-pressure, high-temperature storage containers (accumulators) are dedicated to the separator pressure regulating pump for this purpose. Pressure, temperature and composition of the fluids in these containers are kept close (or identical) to those of the separator.

Accurate regulation of the back pressure leads to more reliable displacements in the core sample, which in turn leads to more accurate measurement of single and multiphase flow properties (from which the relative permeabilities derive). Further, reduced variation in the pressure of the separator decreases the amount of compression that the injection pumps have to generate in order to provide pulse-free flow at the inlet of the core sample, for both steady- and unsteady-state, full re-circulation flow experiments.

The present core-flooding system allows all fluids to be re-circulated over a large range of flow rates, while an accurate and stable back pressure is maintained. This not only creates a much more stable equilibrium between the phases throughout the system, but also minimizes the need for additional fluids.

Reference will now be made in detail to the present embodiment of the invention, an example of which is illustrated in the accompanying drawing. Turning now to FIG. 1, shown is a schematic diagram of an embodiment of apparatus, 10, for multiphase core-flooding that includes twelve cylinder Quizix pumping system (5000 and 6000 series), two each for gas, 12a, 12b, oil, 14a, 14b, and brine, 16a, 16b, for providing these fluids at chosen flow rates and pressures individually, or in various combinations to Hassler-type, cylindrical core holder (having an axis of symmetry), 18, having several fluid connections and containing core, 20, through two-way, manual valves, 22, 24, and 26, respectively; two backpressure regulation pumps, 28a, 28b, for backpressure regulation of core holder 18; two fluid/pressure compensation pumps, 30a, 30b, which, through pneumatic three-way valves, 32a, and, 32b, respectively, and in cooperation with parallel-connected compensation containers or accumulators, 34a, 34b, through two-way manual valve, 36, add or withdraw fluids from acoustic, three-phase separator, 38; and overburden pressure pump, 40, for providing pressure to the exterior of core 20, through three-way pneumatic valve, 42, and two-way manual valve, 44. Gas viscometer, 46, oil viscometer, 48, and brine viscometer, 50, are disposed in-line with pumps 12a, 12b, 14a, 14b, and 16a, 16b, respectively. Convection ovens, 52, 54, and 56, maintain pumps 12a,12b, 14a,14b, 16a,16b, and 28a,28b, and viscometers 46, 48, and 50, accumulators 34a, 34b, and phase separator 38, at individually chosen temperatures, respectively. Holes in the body of these ovens permit passage of fluid flow lines to the core holder and to and from the separator.

In FIG. 1, solid lines represent ⅛ in. tubing, small dashed lines represent ¼ in. tubing, and large dashed lines represent 1 in. tubing. Differential pressure transducers are represented by "DPT", gauge pressure transducers, by "PT", thermocouples by "T", rupture disks by "RD", pressure gauges by "X", and gas cylinders and liquid buckets are marked as such. All parts of the apparatus exposed to flooding fluids are constructed of Hastelloy and other corrosion resistant materials. Apparatus 10 is a closed-loop system that permits fluid to be injected/co-injected into the core at elevated temperatures and pressures.

Cores 20 are placed in a Hassler type core holders 18 having a sleeve, not shown in FIG. 1, and spiral Hastelloy distribution end plugs having four holes, not shown in FIG. 1, each hole being connected to a section of ⅛" Hastelloy tubing.

A dual-cylinder 5000 Quizix pump ($16a,16b$) was used for injection of brine, and two dual-cylinder 6000 Quizix pumps for injection of oil ($14a,14b$) and gas ($12a,12b$). Each cylinder in the 5000 series has a volume of 9.3 cm$^3$, while those for the 6000 series have a volume of 275 cm$^3$. Maximum flow rates for each of these pumps are 15 and 200 cm$^3$/min, respectively. As stated hereinabove, in order to maintain a stable, constant backpressure, dual-cylinder 6000 Quizix pump ($28a,28b$) was used, as opposed to a customary backpressure regulator. As will be discussed hereinbelow, this has allowed achievement and maintenance of stable backpressures at high flow rates over a large range of fluid viscosities, leading to superior equilibrium between fluids in partially miscible or miscible experiments, and more reliable displacements in immiscible experiments, as examples.

To achieve closed-loop, full fluid recirculation capability, the effluent from core 20 is directed to port, 58, of 3,500 cm$^3$ Hastelloy acoustic, three-phase separator 38, which is placed in mechanical convection oven 54, through two-way manual valves, 60, and, 62, and three-way pneumatic valves, 64, and, 66. The levels of the fluids contained therein are monitored using a guided-wave liquid level and interface transmitter to prevent withdrawal of an incorrect fluid into the injection pumps since pumps injecting fluids into the core also withdraw fluids from separator 38. The pressure of the separator is controlled by a compensation module that includes dual-cylinder 6000 Quizix pumps $30a,30b$, and two parallel-connected 2,000 cm$^3$ Hastelloy compensation accumulators $34a$, $34b$. These pumps are heated using heating tape, $68a,68b$, while accumulators $34a,34b$ are located in a third mechanical convection oven. To prevent heat loss, efficient insulation material was applied. Ultra-high molecular weight seals were used throughout in the Quizix cylinders to prevent leakage when working with gases such as $CO_2$.

Overburden pressure was maintained using dual-cylinder 5000 Quizix pump 40, heated using heating tape, 70, which enables automatic adjustment of overburden pressure when the pore pressure is varied, and is advantageous for experiments with rock samples showing sensitivity to such pressures.

Figure 2:
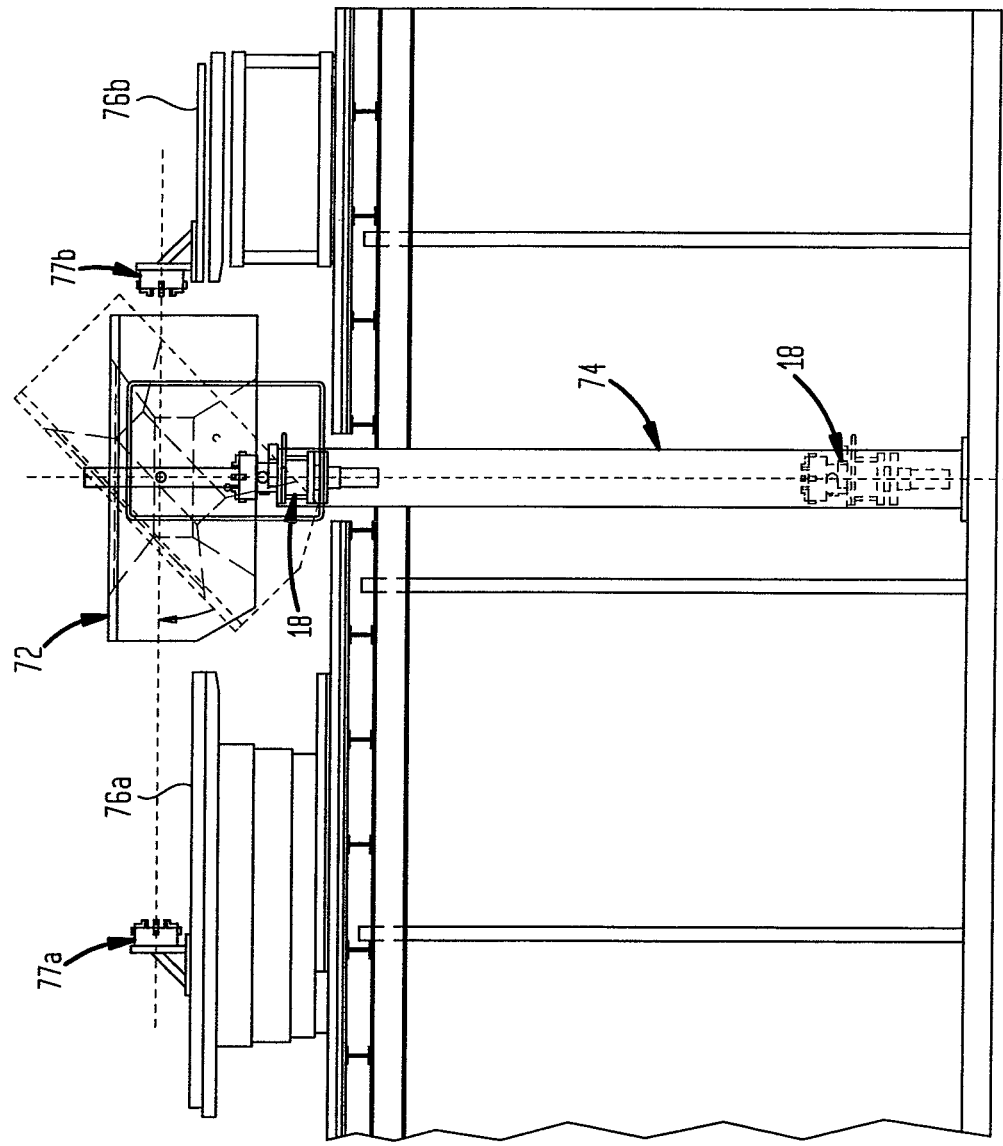
FIG. 2 is a schematic representation of a side view of an embodiment of the computed tomography (CT) scanner and vertical positioning system for locating a core in the scanner, thereby permitting in-situ saturation measurements under flow conditions to be performed.

FIG. 2 is a schematic representation of a side view of an embodiment of the computed tomography (CT) scanner and vertical positioning system for locating a core in the scanner, thereby permitting in-situ saturation measurements under flow conditions to be performed. Medical CT scanner, 72, retrofitted for petrophysical applications, is rotated to the horizontal orientation for permitting core holder 18 to be precisely located therein, and analyses to be performed on vertically-placed rock samples, which was found to reduce gravity segregation effects. Vertical positioning system, 74, was used to move core holder 18 vertically from below into a gantry in CT scanner 72. During a measurement with core sample 20, vertical positioning system 74 is synchronized with horizontal table, $76a,76b$, of scanner 72, using alignment device, $77a,77b$, which synchronization was maintained until each set of measurements (scans at various positions along the length of the core) was completed; that is, until new core 20 is placed in core holder 18. Measurements may be made on both horizontally- and vertically-oriented core samples by orienting the scanner at either 90° or 0° relative to the horizontal table, respectively.

The Quizix pumps and the vertical positioning system are powered by a full-redundancy Liebert uninterruptible power source, not shown in the FIGURES since each group of experiments can take as long as several weeks to complete. Utilization of a reliable emergency power system protects the continuity of flow during a measurement, and the synchronization of the vertical positioning system with the scanner.

In advance of the measurements, the core flood systems are pressure calibrated and tested for possible leaks. To accomplish this, the pumps are connected to atmospheric pressure to make certain that their transducers measure zero gauge pressure. At this point, an accurate reference gauge pressure transducer is connected to the system. The core-flood apparatus is saturated with water and pressurized using one of the pump cylinders until 9,500 psig pressure is read on the reference pressure transducer. At this point, all the pump transducers are set to read 9,500 psig. During this process, the apparatus is leak tested such that a chosen pressure can be maintained for 24 h. All pump transducers are thus calibrated to read pressures relative to the same reference.

The apparatus of FIG. 1 may be operated as follows. Core flooding apparatus 10 is first saturated with fluids; that is, separator, 38, may be filled with brine, oil, and gas, while compensation accumulators, $34a$, and $34b$, are filled with brine and gas only. The apparatus is then pressurized (with additional gas) and heated to a chosen pressure and temperature. Brine pump $16a,16b$, oil pump $14a,14b$, and gas pump $12a,12b$, are used to extract brine, oil, and gas, respectively, from separator 38 and inject them into junction, 100, through two-way manual valves, 102, 104, and 106, respectively, and two-way manual valve, 108, with valves 26, 24, and 26, respectively, closed. This allows brine, oil, and gas to mix at the junction and flow, by-passing core holder, 18, into back pressure pump, $28a,28b$. The above-mentioned full recirculation of the fluids was continued (by-passing core holder 18) for 12-36 h, as an example, under the chosen pressure and temperature of the experiment. This technique was used to achieve equilibrium between the fluids before core flooding is begun. The fluids are in continuous contact in separator 38, compensation accumulators $34a,34b$, flow lines, and back pressure pump $28a,28b$ during a flow initiation process.

The brine, oil, and gas pumps are operated in a paired, constant flow rate mode, permitting the generation of a continuous flow of these fluids. The fluids by-passing core-holder 18 are received by back-pressure pump $28a,28b$ in a paired, constant pressure mode, the pressure at which pump $28a,28b$ is adjusted for receiving fluids being termed the back pressure. This procedure produces a high quality of back pressure regulation at the outlet of core 20 leading to stable pressures throughout the core-flooding system, reliable displacements in the core sample, and also superior equilibrium between the fluids in the system. When receiving cylinder, $110a$, of back pressure pump $28a$ is filled, receiving cylinder, $110b$, of pump $28b$ automatically receives the fluids at the same chosen pressure. The control parameters of the cylinders are adjusted such that this transition takes place smoothly without introducing any pressure pulses into the core sample. That is, cylinder $110b$ is empty and pressurized to the chosen pressure before the transition occurs. After the transition, cylinder $110a$ automatically injects its contents (a mixture of oil, brine and gas) into the bottom of the middle column 58 of separator 38.

Each of cylinders $110a$ and $110b$ has a volume of 275 cm$^3$ and, therefore, introduction of this amount of fluid into fixed-volume separator 38 could lead to a significant increase in its pressure, and changes in the equilibrium conditions of the separator and the experiment may occur. This difficulty can be exacerbated if experiments are carried out at high flow-rates. To avoid this problem, a pressure compensation system that includes a dual-cylinder Hastelloy Quizix pumps $30a,30b$, and the two, parallel-connected, 2,000 cm$^3$ compensation accumulators (4,000 cm$^3$ total volume) $34a,34b$ were added to the apparatus. Both the pumps and the accumulators are pressurized to the chosen pressure and temperature conditions of the experiment. When pump 28*a* commences injection of its contents into separator 38, compensation pump 30*a*,30*b* begins withdrawing brine (the densest fluid) from the bottom of the middle column, 112, of the separator, 38 (different port form the one used by pump 28*a*,28*b*), such that the pressure of the separator remains approximately constant at the chosen pressure which is the same as the back pressure at the outlet of the core sample maintained by pump 28*a*,28*b*. The brine taken from the separator either remains in pump 30*a*,30*b* or is introduced into compensation accumulators 34*a*,34*b*. The large volume of separator 38 (3,500 cm$^3$), assists in the prevention of significant fluctuations in its pressure during this process.

As stated, by keeping the pressure of separator 38 constant, a stable equilibrium will be maintained. To do this accurately, pump 30*a*,30*b* is operated in a bi-directional, paired constant-pressure mode, which permits the pump not only to withdraw brine as discussed hereinabove, but also to inject brine into the separator in the event that the pressure of the separator drops below a chosen set point. This may occur under two conditions: 1) if separator 38 experiences negative accumulation of fluids with a reduction in the pressure therein since continuous withdrawal of fluids from separator 38 by pumps 12*a*,12*b*, 14*a*,14*b*, and 16*a*,16*c*, and intermittent injection of fluids into separator 38 by pump 28*a*,28*b*, are not necessarily synchronized; and 2) if leakage takes place in core-flooding system 10, the replacement fluids derive from separator 38, which may lead to reduction in the pressure therein. In both of these situations, separator 38 is provided with compensation brine by pump 30*a*,30*b*, and accumulators 34*a*,34*b* to maintain its pressure at the chosen set point. The fluid levels in separator 38 are continuously monitored using guided-wave radar liquid level and interface transmitters to make certain that pumps 12*a*,12*b*, 14*a*,14*b*, and 16*a*,16*b* will not withdraw the incorrect fluids. Minimization of the pressure variations in the back pressure and pressure of the separator achieve and maintain equilibrium between the fluids and establish the desired displacement in the core-sample.

After the three fluids (oil, gas, and brine) are re-circulated, by-passing the core sample, for a sufficiently long time that the fluids are equilibrated, the fluids and the apparatus are ready to inject fluids into the sample. Generally, core sample 20 saturated with equilibrated brine, and core-flooding apparatus 10 can then simultaneously inject one, two, or three of the fluids into the core at various flow rates allowing various displacement mechanisms to be investigated. Computed tomography (CT) scanner 72, scans core 20 during the measurements to obtain 3D, in-situ saturation data. As stated, most of the flow experiments were carried out while cylindrical core holder 18 was placed such that its axis of symmetry was vertically disposed inside the CT scanner. Fluids were injected from either the top or bottom of core holder 18 and produced from the opposite end thereof.

Figure 3:
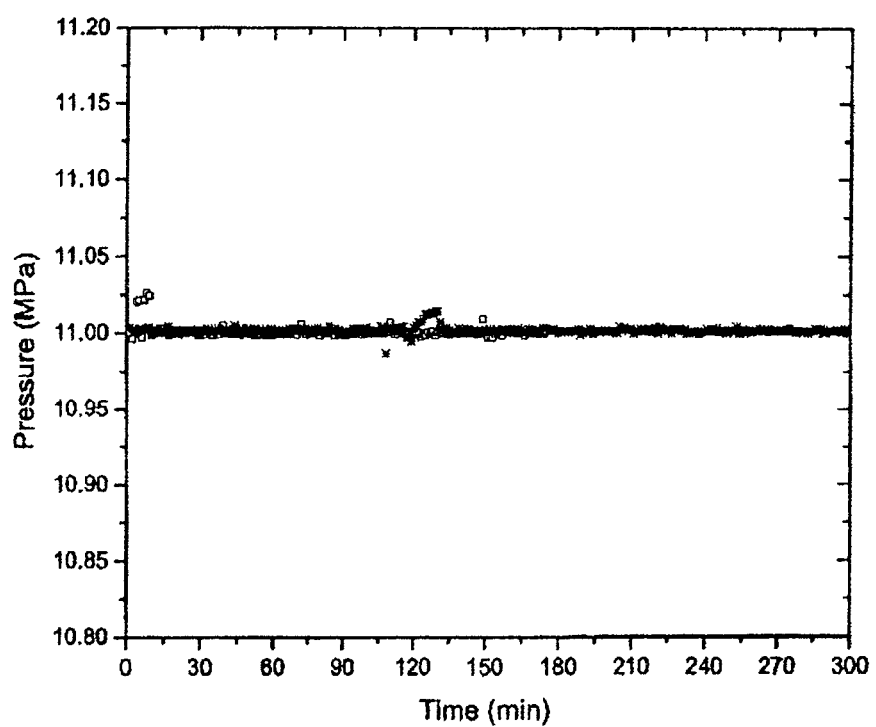
FIG. 3 is a graph of the backpressure (MPa) as a function of time (min.) for two cores investigated.

FIG. 3 is a graph of the backpressure (MPa) as a function of time (min.) for two cores investigated, and demonstrates the stability of the backpressure during the separate injection of brine and carbon dioxide into core 20 in core holder 18. As stated, core-flooding system 10 is a closed-loop apparatus, and is operated under full-recirculation condition, showing very stable pressures and therefore maintenance of equilibrium conditions between the fluids.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A recirculating, constant backpressure apparatus for flooding a core with at least one chosen fluid, comprising:
    a core holder for containing said core and having a longitudinal axis, an inlet port for introducing the at least one fluid into contact with said core, an outlet port, and a port for applying a chosen pressure to an exterior surface of said core;
    an overburden pressure pump in fluid connection with the pressure port of said core holder;
    at least one fluid pump for pumping the at least one chosen fluid in fluid communication with the inlet port of said core holder;
    a separator for separating the at least one fluid from said at least one fluid pump by density thereof from other fluids exiting the core holder after having passed through said core, said separator having a first bottom port, a second bottom port, and at least one fluid return port for returning fluid to said at least one fluid pump;
    a backpressure pump in fluid communication with the outlet port of said core holder for maintaining a chosen back pressure at the outlet port of said core holder, and in fluid communication with the first bottom port of said separator for transferring the at least one fluid exiting said core holder to said separator; and
    a pressure compensation pump in fluid communication with the second bottom port of said separator for preventing a change in pressure as the at least one fluid is transferred to said separator by said back-pressure pump.

2. The apparatus of claim 1, where pressure in said separator is controlled by said pressure compensation pump by removing or adding the densest fluid of the at least one fluid from the second bottom port of said separator.

3. The apparatus of claim 1, wherein said at least one fluid pump is a dual-cylinder pump, whereby said at least one fluid is removed from said separator as said at least one fluid is injected into said core holder by said at least one fluid pump.

4. The apparatus of claim 3, wherein said at least one fluid pump is operated in a constant flow rate mode.

5. The apparatus of claim 1, wherein said at least one chosen fluid is selected from oil, brine and a gas.

6. The apparatus of claim 5, wherein the gas is chosen from carbon dioxide, nitrogen, methane, sulfur dioxide, and nitrogen dioxide, and mixtures thereof.

7. The apparatus of claim 1, wherein said separator comprises an acoustic separator.

8. The apparatus of claim 7, wherein phase boundaries for said at least one chosen fluid and other fluids in said separator are determined using a guided-wave liquid level and interface transmitter.

9. The apparatus of claim 1, further comprising a computer tomography scanner for measuring x-ray attenuation of fluids in said core, whereby saturation of the at least one fluid is determined.

10. The apparatus of claim 9, wherein the x-ray attenuation measurement is made under fluid flow conditions.

11. The apparatus of claim 9, wherein the longitudinal axis of said core holder is oriented in the vertical direction.

12. The apparatus of claim 11, further comprising a vertical core positioning apparatus for adjusting the position of said core in said computer tomography scanner.

13. A method for flooding a core by recirculating at constant backpressure at least one chosen fluid through said core, comprising the steps of:
    pumping the least one fluid through a core in a core holder having a longitudinal axis, using at least one fluid pump;
    pressurizing the exterior surface of the core to a chosen pressure;
    separating the at least one fluid by density thereof from other fluids exiting the core holder after having passed through the core, in a separator;
    returning the at least one fluid to the at least one pump, after said step of separating the at least one fluid;
    maintaining a chosen backpressure for the at least one fluid exiting the core holder; and
    removing fluid from or adding fluid to the separator to prevent an increase or decrease in backpressure, respectively, in said step of separating the at least one fluid.

14. The method of claim 13, wherein pressure in the separator is controlled by removing or adding the densest fluid of the at least one fluid from the bottom of the separator.

15. The method of claim 13, wherein the at least one fluid pump is a dual-cylinder pump, whereby the at least one fluid is removed from the separator as the at least one fluid is injected into the core holder by the at least one fluid pump.

16. The method of claim 15, wherein the at least one fluid pump is operated in a constant flow rate mode.

17. The method of claim 13, wherein the at least one chosen fluid is selected from oil, brine and a gas.

18. The method of claim 17, wherein the gas comprises carbon dioxide, nitrogen, methane, sulfur dioxide, and nitrogen dioxide, and mixtures thereof.

19. The method of claim 13, wherein the separator comprises an acoustic separator.

20. The method of claim 19, wherein phase boundaries for the at least one chosen fluid and other fluids in the separator are determined using a guided-wave liquid level and interface transmitter.

21. The method of claim 13, further comprising the step of measuring x-ray attenuation of fluids in the core, whereby saturation of the at least one fluid is determined.

22. The method of claim 21, wherein said step of measuring x-ray attenuation is performed using a computer tomographic scanner.

23. The method of claim 22, wherein the x-ray attenuation measurement is made under fluid flow conditions.

24. The method of claim 22, wherein the longitudinal axis of the core holder is oriented in the vertical direction.

25. The method of claim 24, further comprising the step of adjusting the position of the core in the computer tomography scanner, whereby multiple scans along a length of the core are obtained.

* * * * *